(12) United States Patent
Gilkerson et al.

(10) Patent No.: US 7,697,993 B2
(45) Date of Patent: Apr. 13, 2010

(54) METHOD AND APPARATUS FOR QUESTION-BASED PROGRAMMING OF CARDIAC RHYTHM MANAGEMENT DEVICES

(75) Inventors: James O. Gilkerson, Stillwater, MN (US); Richard Milon Dujmovic, Jr., Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 378 days.

(21) Appl. No.: 10/844,642

(22) Filed: May 13, 2004

(65) Prior Publication Data

US 2005/0256550 A1 Nov. 17, 2005

(51) Int. Cl.
*A61N 1/00* (2006.01)
(52) U.S. Cl. ............... 607/59; 607/30; 607/31
(58) Field of Classification Search ........ 607/30, 607/31, 32, 59, 60; 128/903
See application file for complete search history.

(56) References Cited

U.S. PATENT DOCUMENTS

| | | | |
|---|---|---|---|
| 5,292,341 A | 3/1994 | Snell | |
| 5,360,437 A | 11/1994 | Thompson | |
| 5,716,382 A * | 2/1998 | Snell | 607/30 |
| 5,722,999 A | 3/1998 | Snell | |
| 5,817,137 A * | 10/1998 | Kaemmerer | 607/59 |
| 6,088,617 A * | 7/2000 | Arand et al. | 607/5 |
| 6,110,108 A * | 8/2000 | Shimura et al. | 128/903 |
| 6,168,563 B1 * | 1/2001 | Brown | 600/301 |
| 6,482,154 B1 | 11/2002 | Haubrich et al. | |
| 6,522,925 B1 * | 2/2003 | Gilkerson et al. | 607/30 |
| 6,648,823 B2 | 11/2003 | Thompson et al. | |
| 6,690,972 B2 | 2/2004 | Colney et al. | |
| 7,110,818 B2 | 9/2006 | Anderson et al. | |
| 2002/0169488 A1 | 11/2002 | Limousin et al. | |

(Continued)

FOREIGN PATENT DOCUMENTS

EP 1184050 A2 3/2002

(Continued)

OTHER PUBLICATIONS

Kenknight, Bruce H., et al., "System and Method for Determining Patient-Specific Implantable Medical Device Programming Parameters", U.S. Appl. No. 10/950,876, filed Sep. 27, 2004, 29 pgs.

*Primary Examiner*—Carl H Layno
*Assistant Examiner*—Yun Haeng Lee
(74) *Attorney, Agent, or Firm*—Schwegman, Lundberg & Woessner, P.A.

(57) ABSTRACT

A cardiac rhythm management (CRM) system includes a programming device that identifies the device type of an implantable medical device, selects a predetermined questioning sequence based on the device type, and interacts with a user through a user interface screen by conducting a question-and-answer session according to the predetermined questioning sequence. After displaying a question and receiving an answer to the question, the programming device sets one or more programmable parameter values and/or displays a follow-up question in response to the answer. The programming device also allows the user to enter one or more programmable parameter values directly during or after the question-and-answer session. The implantable medical device is programmed to operate in one or more operational modes based on at least the answers received from the user during the question-and-answer session and the parameter values entered by the user, if any.

31 Claims, 5 Drawing Sheets

U.S. PATENT DOCUMENTS

2003/0171791 A1* 9/2003 KenKnight et al. ............ 607/60
2004/0181262 A1* 9/2004 Bauhahn ....................... 607/48
2005/0245992 A1* 11/2005 Persen et al. .................. 607/60
2006/0241712 A1 10/2006 Cates et al.

FOREIGN PATENT DOCUMENTS

WO WO-2006113890 A2 10/2006

* cited by examiner

METHOD AND APPARATUS FOR QUESTION-BASED PROGRAMMING OF CARDIAC RHYTHM MANAGEMENT DEVICES

FIELD OF THE INVENTION

This document generally relates to cardiac rhythm management (CRM) systems and particularly, but not by way of limitation, to method and apparatus for programming implantable CRM devices.

BACKGROUND

Implantable CRM devices such as pacemakers and defibrillators are used to treat cardiac arrhythmias, heart failure, and other cardiovascular disorders by delivering electrical energy to the heart. Advances in biomedical technology have provided implantable CRM devices with increasingly sophisticated features and operational modes adaptive to a patient's changing physiological conditions and individualized lifestyle. As a consequence, programming an implantable CRM device has become an increasingly complicated task for the users including healthcare professionals.

To operate in a patient after implantation, an implantable CRM device is programmed by a user using an external programming device. The programming device includes a user interface that allows the user to observe the patient's conditions indicated by signals acquired by the implantable CRM device and to program the implantable CRM device by entering or selecting a series of programmable parameters. Such parameters include, but are not limited to, therapy modes and quantitative parameters required for operating in each therapy mode, special features and quantitative parameters required for utilizing each special feature, and various therapy activation or feature activation criteria. Additionally, devices of different types, as well as some devices of the same type, require different programmable parameters and/or different programming procedures. The user may have to receive extensive training on how to program each specific type of implantable CRM devices and may have to spend months or even years before being able to optimally utilize many advanced features. Introductions of new device features, while providing the users with additional power in treating cardiovascular diseases, tend to make the programming of implantable CRM devices more intimidating. One undesirable consequence is underutilization of available device features and capabilities. If properly utilized, such underutilized device features and capabilities will potentially provide substantial additional benefits to many patients who have already benefited from implantable CRM devices.

For these and other reasons, there is a need to provide healthcare professionals with a user-friendlier device for programming implantable CRM devices.

SUMMARY

A CRM system includes a programming device that identifies the device type of an implantable medical device, selects a predetermined questioning sequence based on the device type, and interacts with a user through a user interface screen by conducting a question-and-answer session according to the predetermined questioning sequence. The programming device also allows the user to enter one or more programmable parameter values directly during or after the question-and-answer session. The implantable medical device is programmed to operate in one or more operational modes based on at least the answers received from the user during the question-and-answer session and the parameter values entered by the user, if any.

In one embodiment, a medical device programmer includes a telemetry circuit, a device identification device, a user interface with a user-controllable programming mode switch and a screen, and a parameter generator. The telemetry circuit communicates with an implantable medical device. The device identification device identifies a device type of the implantable medical device based on information received by the telemetry circuit from the implantable medical device. The device type is indicative of one or more available operational modes of the implantable medical device. The user-controllable programming mode switch allows a user to select one of a question-based programming mode and a parameter-based programming mode and to switch between these two programming modes. When the question-based programming mode is selected, the screen includes at least a question field and an answer field. When the parameter-based programming mode is selected, the screen includes a plurality of parameter value entry fields. The parameter generator produces values for a set of operational parameters for the implantable medical device to operate in at least one of its one or more available operational modes.

In one embodiment, communication with an implantable medical device is established. Information indicative of a device type of the implantable medical device is received from the implantable medical device. The device type is indicative of one or more available operational modes of the implantable medical device. A predetermined questioning sequence is selected based on the device type. According to the predetermined questioning sequence, a first question is generated and presented, and a first answer to the first question is received. Then, further questions are generated and presented, and further answers to the further questions are received, according to the predetermined questioning sequence. At least one operational mode is selected from the one or more available operational modes of the implantable medical device based on at least one answer of the first answer and the further answers. Values for a set of operational parameters associated with the at least one operational mode are generated based on at least the first answer and the further answers.

In one embodiment, a device type of an implantable medical device is identified. The device type is indicative of one or more available operational modes of the implantable medical device. A selection of one of a question-based programming mode and a parameter-based programming mode is received from a user. If the question-based programming mode is selected, a sequence of questions is presented with an answer field for each question to receive answers to the sequence of questions. If the parameter-based programming mode is selected, a plurality of parameter value entry fields is presented to receive parameter values. Values for a set of operational parameters are produced based on at least one of the answers to the sequence of questions and the received parameter values. The set of operational parameters is associated with at least one operational mode selected by the user from the one or more available operational modes of the implantable medical device.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are for illustrative purposes only and not necessarily drawn to scale, like numerals describe similar components throughout the several views. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this document are not necessarily to the same embodiment, and such references contemplate more than one embodiment. In this document, a "user" includes a healthcare professional including a physician or other caregiver.

This document discusses a question-based programming method and programming device for an implantable medical device. The programming device interacts with a user by conducting a question-and-answer session according to a questioning sequence developed based on a programming decision tree. The decision tree is developed based on the features and capabilities of the implantable medical device and allows for optimization of device operation based on a patient's individual conditions and needs. After displaying a question to the user and receiving an answer to the question from the user, the programming device sets one or more programmable parameters and/or displays a follow-up question in response to the answer. The questions are primarily in terms familiar to or easily understood by users who are healthcare professionals. The answers are based on, for example, the patient's medical record and examinations performed by the user. A programming session is completed when the implantable medical device is believed to be optimally programmed based on at least the decision tree and the user's answers. Other information obtained by the programming device, such as one and more signals acquired using the implantable medical device, is also utilized in programming the implantable medical device. The programming device allows the user to optimally utilize the device features and capabilities based on the patient's specific conditions, usually without extensive training and/or extensive experience.

Figure 1:
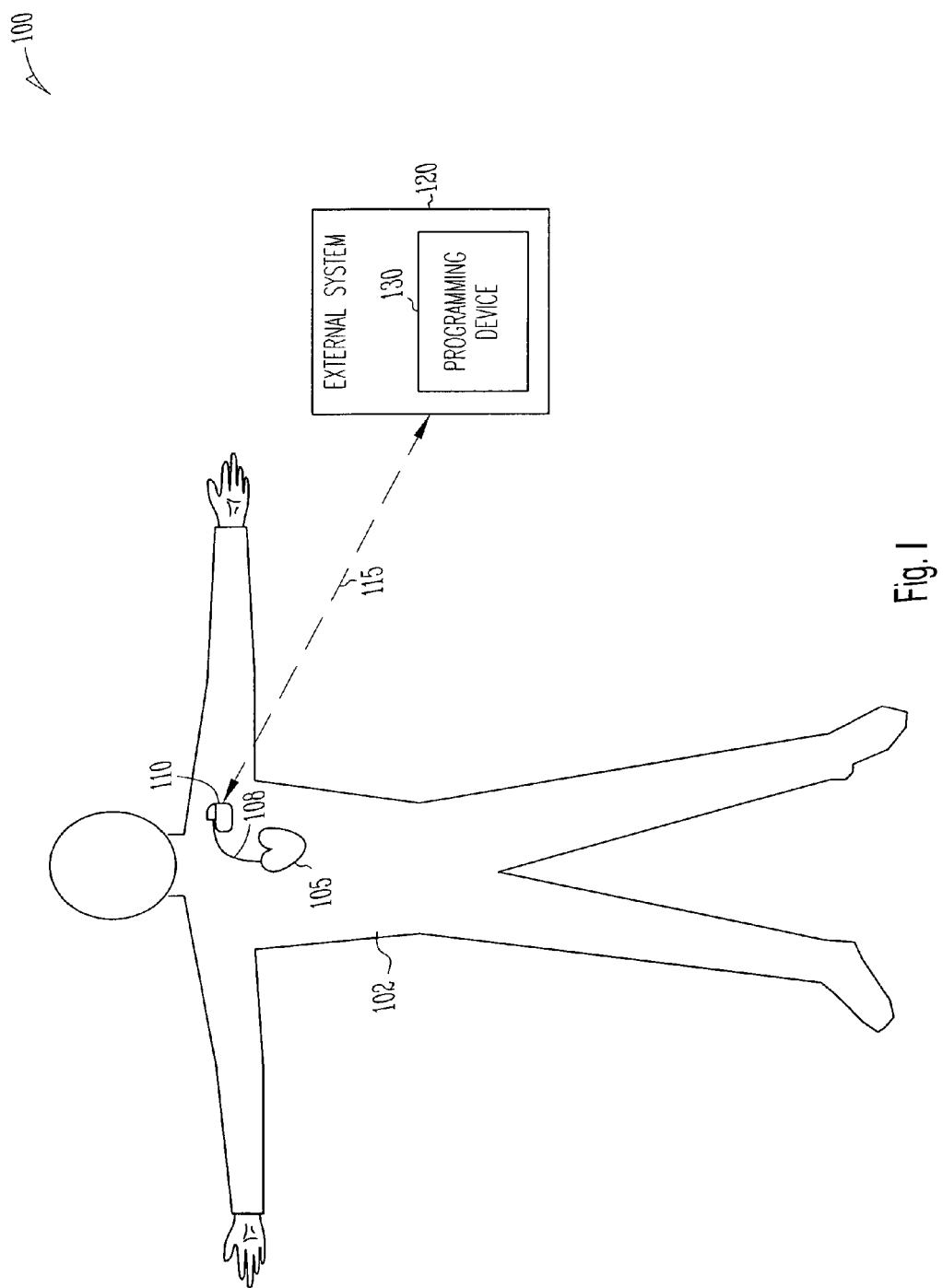
FIG. 1 is an illustration of one embodiment of a CRM system including an implantable medical device and portions of the environment in which the CRM system is used.

FIG. 1 is an illustration of one embodiment of a CRM system 100 and portions of the environment in which CRM system 100 is used. System 100 includes an implantable medical device 110, a lead system 108, an external system 120, and a wireless telemetry link 115.

After implantation, implantable medical device 110 operates within a body 102 to sense activities of a heart 105 and deliver one or more therapies to heart 105. Implantable medical device 110 includes, but is not limited to, one or more of a pacemaker, a cardioverter/defibrillator, a cardiac resynchronization therapy device, a cardiac remodeling control therapy device, a drug delivery device, and a biological therapy device. A device type of implantable medical device 110 indicates its available operational modes each corresponding to one type of therapy delivery. For example, a particular type of implantable medical device 110 includes an implantable pacemaker/defibrillator providing for operational modes including a bradycardia pacing mode, an anti-tachycardia pacing mode, and a defibrillation mode. Each operational mode is associated with a plurality of operational parameters. Values for a set of operational parameters are programmed into implantable medical device 110 for it to operate in one or more operational modes selected by the user.

Lead system 108 provides one or more electrical and/or other connections between implantable medical device 110 and heart 105. In one embodiment, lead system 108 includes one or more pacing and/or defibrillation leads each having one or more electrodes for electrogram sensing and/or delivery of electrical pulses to heart 105. In one embodiment, one or more intracardiac sensors are incorporated into lead system 108 to sense signals such as heart sounds, intracardiac pressures, and chemical parameters of the blood.

External system 120 communicates with implantable medical device 110 through telemetry link 115. It allows the user and/or the patient to communicate with implantable medical device 110. External system includes a programming device 130 that allows the user to program implantable medical device 110. Programming device 130 provides for a question-based programming mode and a parameter-based programming mode. When operating in the question-based programming mode, programming device 130 asks the user a sequence of questions. Based on at least the answers to these questions, programming device 130 determines the values for the set of operational parameters for programming implantable medical device 110 to operate in one or more of its operational modes. When operating in the parameter-based programming mode, programming device 130 presents parameters used in its one or more current operational modes with their current values and allows the user to adjust the current values. In one embodiment, the user may choose either programming mode to start a programming session and switch between the two programming modes during the programming session.

In one embodiment, external system 120 includes an external programmer. The external programmer includes programming device 130. In another embodiment, external system 120 is a patient management system including an external device, a telecommunication network, and a remote device. The external device is placed within the vicinity of implantable medical device 110 and communicates with implantable medical device 110 bi-directionally via telemetry link 115. The remote device is in a remote location and communicates with the external device bi-directionally through the telecommunication network, thus allowing the user to monitor and treat the patient from a distant location. In one specific embodiment, the external device includes programming device 130. In another specific embodiment, the remote device includes programming device 130.

Telemetry link 115 provides for data transmissions between implantable medical device 110 and external system 120. In one embodiment, telemetry link 115 is an inductive telemetry link. In an alternative embodiment, telemetry link 115 is a far-field radio-frequency telemetry link. Telemetry link 115 provides for data transmission from implantable medical device 110 to external system 120. This may include, for example, transmitting information indicative of the device type of implantable medical device 110, transmitting data indicative of the current operational mode(s) and parameter values, transmitting real-time physiological data acquired by implantable medical device 110, extracting physiological data acquired by and stored in implantable medical device 110, extracting therapy history data, and extracting data indicating an operational status (e.g., battery status and lead impedance). Telemetry link 115 also provides for data transmission from external system 120 to implantable medical device 110. This may include, for example, parameters for programming implantable medical device 110 to acquire physiological data, to perform at least one self-diagnostic test (such as for a battery status and lead impedance status), and/or to deliver at least one therapy. The physiological data represent signals acquired by implantable medical device 110. The signals include, but not being limited to, one or more of electrograms, heart sounds or a signal indicative of heart sounds, activity level signal, impedance signal, pressure or pressure-indicating signal, and respiratory signal. In one embodiment, the physiological data also include parameters measured from one or more of these signals. In one embodiment, external system 120 or the user determines parameter values for programming implantable medical device 110 based on these physiological data.

Figure 2:
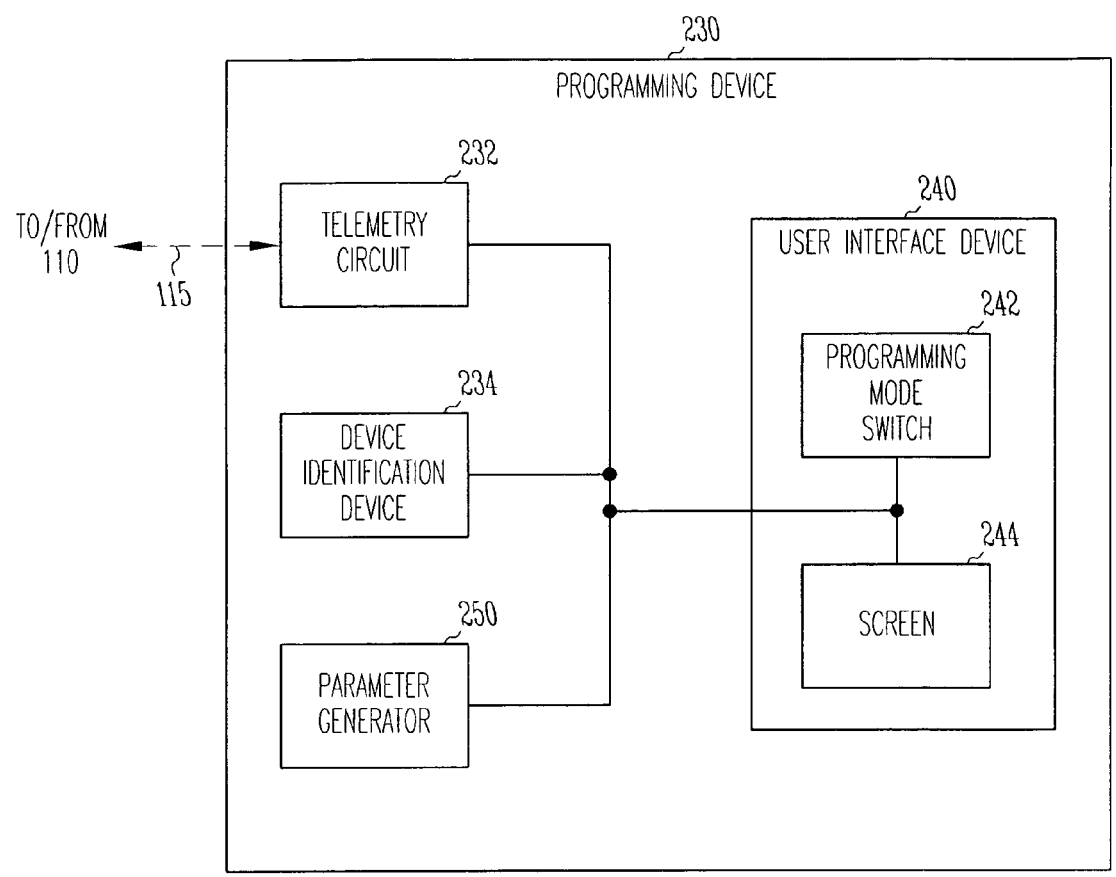
FIG. 2 is a block diagram illustrating one embodiment of a device for programming the implantable medical device.

FIG. 2 is a block diagram illustrating a circuit of a programming device 230, which is one embodiment of programming device 130. Programming device 230 includes a telemetry circuit 232, a device identification device 234, a user interface 240, and a parameter generator 240.

Telemetry circuit 232 provides programming device 230 with its capability of communicating with implantable medical device 110 via telemetry link 115. Device identification device 234 identifies the device type of implantable medical device 110. In one embodiment, upon establishment or activation of the telemetry link 115 at the beginning of a programming or other communication session, device identification device 234 receives information sent from implantable medical device 110 via telemetry link 115. The information indicates the device type, and hence, available operational modes of implantable medical device 110. In one embodiment, device identification device 234 includes a device model identification device to receive a model number from implantable medical device 110 and identifies the device type as indicated by the model number. In another embodiment, device identification device 234 includes a device code identification device to receive a device code, such as a device serial number, from implantable medical device 110 and identifies the device type as indicated by the device code.

User interface device 240 allows the user to program implantable medical device 110 for operating in one or more of its available operational modes. User interface device 240 includes a programming mode switch 242 and a screen 244. Programming mode switch 242 allows the user to select one of the question-based programming mode and the parameter-based programming mode. When the question-based programming mode is selected, screen 244 includes at least one question field to display a question and at least one answer field to receive an answer to the question. In one embodiment, the answer field includes buttons each corresponding to an answer of a plurality of predetermined possible answers. In another embodiment, the answer field includes a selection menu listing the plurality of predetermined possible answers. In one specific embodiment, the selection menu is a pull-down selection menu. In another specific embodiment, a selection key is provided with each possible answer in the selection menu. In a further embodiment, the answer field also includes a field for entry of the answer by typing or writing, for example, when a question has too many possible answers, such as a quantity measured by the user. When the parameter-based programming mode is selected, screen 244 presents selected parameters associated with a selected operational mode of implantable medical device 110. Each selected parameter is presented with its current value and a parameter value entry field. The parameter value entry field allows the user to update the current value by entering a new value. In one embodiment, the user enters the new value by selecting a value from a list of predetermined of values. In another embodiment, the user types or writes the new value in the parameter value entry field.

Parameter generator 250 controls the presentation and response reception on screen 244 and produces values for all the parameters required for implantable medical device 110 to operate in one or more selected operational modes. These values are transmitted through telemetry circuit 232 and telemetry link 115 to implantable medical device 110 for its programming. Parameter generator 250 produces these values based on at least the answers and/or parameter values received by user interface device 240 by executing a predetermined parameter generation algorithm. Interactions between the parameters are taken into consideration in the development of the parameter generation algorithm. In one embodiment, the values are produced further based on nominal parameter values stored in programming device 230. In one embodiment, the values are produced further based on signals acquired by implantable medical device 110. In this embodiment, programming device 230 provides for optimal programming of implantable medical device 110 by utilizing knowledge and abilities of the system and the user.

Figure 3:
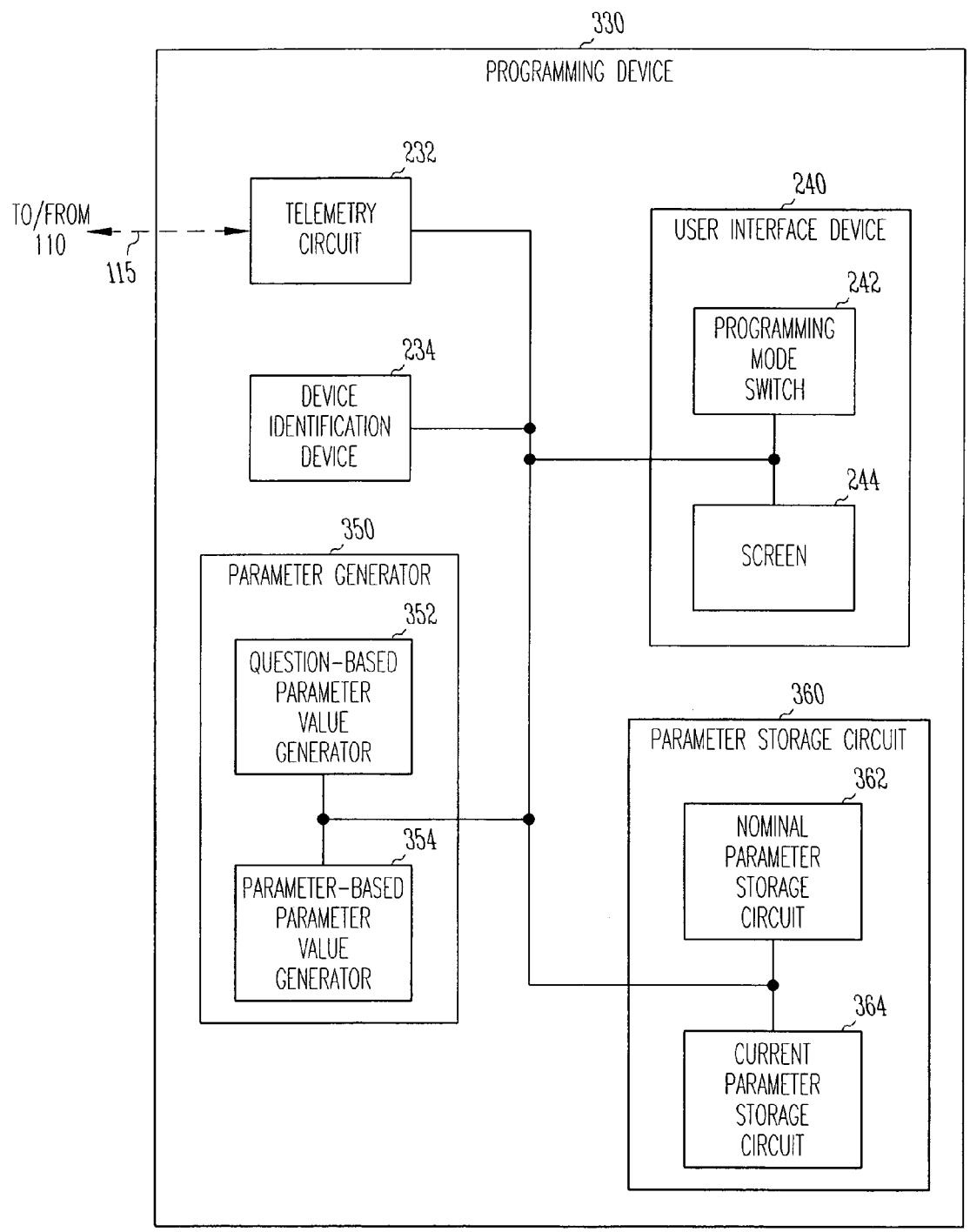
FIG. 3 is a block diagram illustrating another embodiment of the device for programming the implantable medical device.

FIG. 3 is a block diagram illustrating a circuit of a programming device 330, which is another embodiment of programming device 130. Programming device 330 includes telemetry circuit 232, device identification device 234, user interface 240, a parameter generator 350, and a parameter storage circuit 360.

Parameter generator 350 is one embodiment of parameter generator 250 and includes a question-based parameter value generator 352 and a parameter-based parameter value generator 354. When the question-based programming mode is selected, question-based parameter value generator 352 controls the presentation of the questions and the reception of the answers and produces parameter values based on at least the answers and a set of predetermined parameter interaction rules. When the parameter-based programming mode is selected, question-based parameter value generator 352 controls the presentation of parameters with their current values and the reception of new parameter values and produces parameter values based on at least the current and new values and the set of predetermined parameter interaction rules.

Question-based parameter value generator 352 includes a questioning sequence selector, a question generator, an answer receiver, and a question-based value producer. The questioning sequence selector selects a questioning sequence based on the device type of implantable medical device 110. The questioning sequence is selected from a plurality of predetermined questioning sequences each associated with a specific device type. The questioning sequence is designed to determine values for all the operational parameters required for implantable medical device 110 to operate in one or more of its operational modes by conducting a question-and-answer session. In one embodiment, the questioning sequence is developed based on a predetermined programming decision tree and includes branches each corresponding to one operational mode. Each branch includes sub-branches each corresponding to a feature of the operational mode. By following the questioning sequence including the branches and sub-branches, only questions pertaining to the required parameters are asked. Questions from each branch are asked only if the operational mode associated with that branch is selected by answering a preceding question from the questioning sequence. Questions from each sub-branch are asked only if the feature associated with that branch is selected by answering a preceding question from the branch. In one embodiment, the required parameters include all parameters whose values may be optimized for the selected operational mode(s) according to the patient's specific conditions. The question generator generates questions to be presented in the question field of screen 244 according to the selected questioning sequence. The answer receiver receives answers through the answer field. After the first question of the question-and-answer session is generated and the first answer is received, the question generator generates further questions each based on one or more answers received in response to one or more previously presented questions. The question-based value producer produces the required parameter values based on at least the received answers. In one embodiment, the question-based value producer produces the required parameter values after receiving at least the first answer. In another embodiment, the question-based value producer produces the required parameter values after receiving all the answers, i.e., after the selected questioning sequence is completed. In one embodiment, the question-based value producer produces the required parameters based on at least the received answers and predetermined rules, such as rules governing interactions and other relationships between parameters and limitations to parameter values. In one embodiment, the question-based value producer produces the required parameters further based on signals acquired by implantable medical device 110 and/or parameters derived from these signals. The question-and-answer session ends when all the answers required for producing the required parameter values are received from the user.

Parameter-based parameter value generator 354 includes a parameter value receiver and a parameter-based value producer. The parameter value receiver receives new values entered into the parameter value entry fields. The parameter-based value producer produces the required parameter values each based on its current value and the new value, if entered. In one embodiment, the parameter-based value producer produces the required parameters based on at least the current and new values and predetermined rules, such as rules governing interactions and other relationships between parameters and limitations to parameter values.

Parameter storage circuit 360 includes a nominal parameter storage circuit 362 and a current parameter storage circuit 364. Nominal parameter storage circuit 362 stores nominal parameter values for all the parameters programmable using programming device 330. Current parameter storage circuit 364 stores current parameter values, i.e., the values to be used for programming implantable medical device 110. Current parameter storage circuit 364 includes a parameter initialization circuit and a parameter update circuit. The parameter initialization circuit sets each value of the current parameter values to a corresponding nominal parameter when implantable medical device 110 is initialized or reset. The nominal parameter values are used as the current parameter values if parameter generator 350 does not provide a different value after the initialization or reset. The parameter update circuit changes a current parameter value to a corresponding different parameter value produced by parameter generator 350. In one embodiment, current parameter values are updated with parameter values produced by either question-based parameter value generator 352 or parameter-based parameter value generator 354. In one embodiment, if both question-based parameter value generator 352 and parameter-based parameter value generator 354 produce a value for the same parameter, the current parameter value is updated by the value produced by parameter-based parameter value generator 354, i.e., directly entered by the user.

Figure 4:
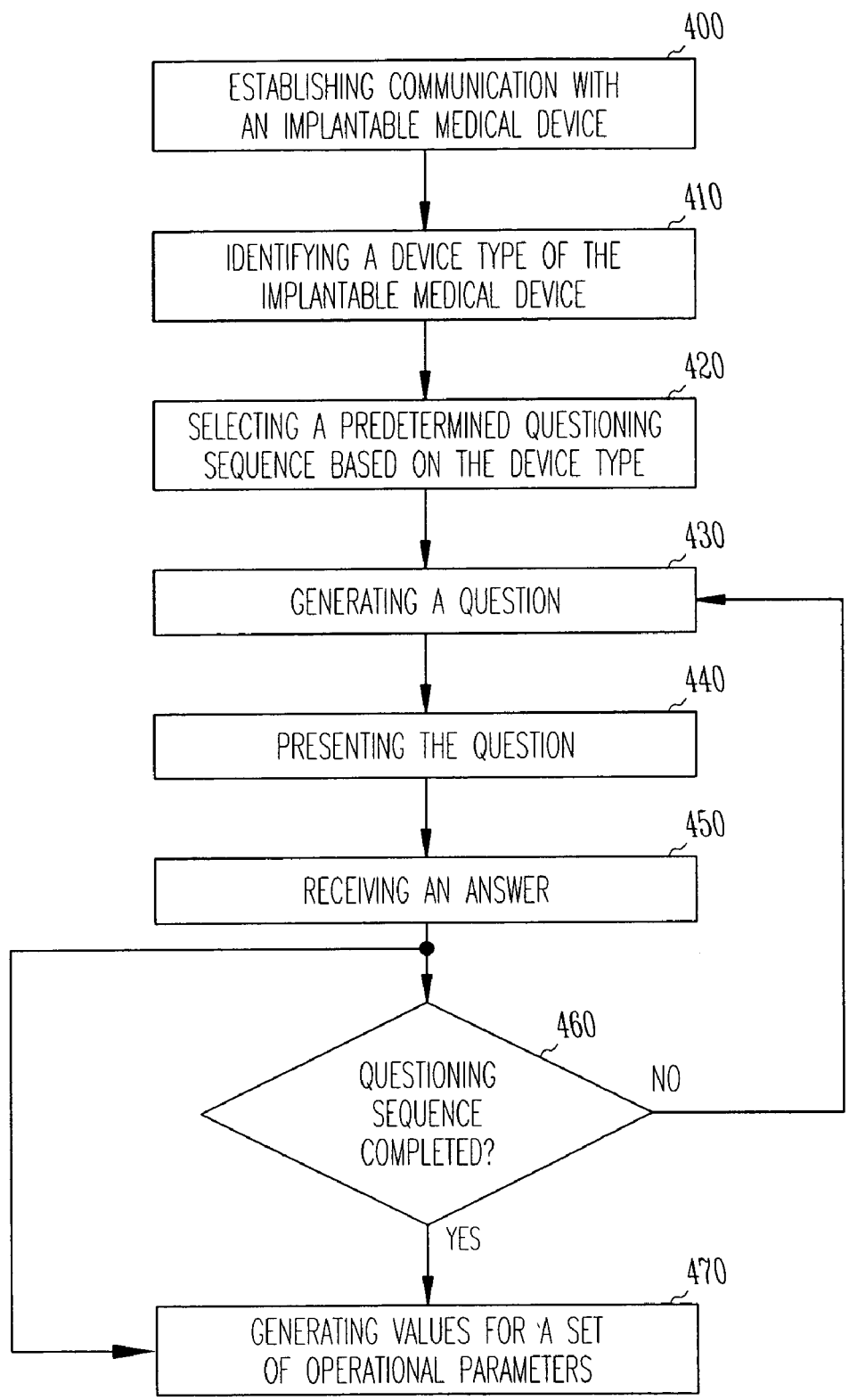
FIG. 4 is a flow chart illustrating one embodiment of a method for programming the implantable medical device.

FIG. 4 is a flow chart illustrating one embodiment of a method for programming an implantable medical device such as implantable medical device 110. In one embodiment, the method is performed by a medical device programmer such as programming device 130, including its various embodiments such as illustrated as programming device 230 or programming device 330.

Communication with the implantable medical device is established at 400, when a programming session for the implantable medical device begins. The implantable medical device is identified at 410. The identification includes identifying a device type of the implantable medical device. The device type indicates the capabilities, or the available operational modes, of the implantable medical device. The device type is indicated by, for example, a model number and/or a device code such as a serial number.

A predetermined questioning sequence is selected based on the device type at 420. The question sequence is designed to generate questions seeking answers that provide a basis for determining parameter values required for operating the implantable medical device to operate in one or more operational modes selected by the user. A question is generated according to the questioning sequence at 430 and presented to a user at 440. An answer to the question is received from the user at 450. If the questioning sequence is not completed at 460, then 430, 440, and 450 are repeated. During the repetitions, one or more questions are each generated based on at least one answer to a question previously generated and presented as part of the questioning sequence. Such a question-and-answer session is conducted by repeating 430, 440, and 450 until the questioning sequence is completed.

Values for a set of operational parameters are generated at 470 based on at least the answers received at 450 (repeatedly). The set of operational parameters allow the implantable medical device to operate to deliver the one or more therapies selected by the user.

In one embodiment, one or more signals are received from the implantable medical device. In one further embodiment, recommended answers are generated for one or more questions based on at least the one or more signals and presented with the one or more questions. In another further embodiment, values for the set of operational parameters are generated at 470 based on at least the answers received at 450 and the one or more signals.

In one embodiment, values for one or more operational parameters are directly entered by the user. Values for the set of operational parameters are generated at 470 based on at least the answers received at 450 and the values directly entered by the user.

In one embodiment, values for the set of operational parameters are initially set to predetermined nominal values. As a result of a programming session, the values are updated with one or more values generated based on at least the answers received at 450 and one or more values directly entered by the user. In one embodiment, if a value for a parameter is generated based on at least an answer received at 450, and another value for the same parameter is directly entered by the user, the parameter is set to the value directly entered by the user.

EXAMPLE

Programming a Pacemaker for Bradycardia Pacing

The following example is intended to illustrate, but not to limit, the present subject matter. It is intended to generally illustrate a question-based programming method according to the present subject matter. In this example, a dual-chamber pacemaker, as one specific embodiment of implantable medical device 110, is implanted in a patient in need of bradycardia pacing therapy, as determined by the user. A programming device such as programming device 130 has established communication with the pacemaker and identified its device type. A questioning sequence is selected based on the device type. The questioning sequence is developed based on a programming decision tree for the pacemaker and includes branches each corresponding to an operational mode and sub-branches each corresponding to a device feature. A question-and-session is conducted according to the questioning sequence, as follows:

Question 1: Which therapy or therapies are needed? (Select all needed therapies.)

Answer 1: (a) Bradycardia pacing, . . . (list of therapies, i.e., operational modes, available according to the device type).

Action in response to Answer 1 if (a) is selected: Select the bradycardia pacing branch of the questioning sequence. Present Question 2 (according to the bradycardia pacing branch of the questioning sequence).

Question 2: Is the patient chronotropically competent?

Answer 2: (a) Yes, (b) No.

Action in response to Answer 2 if (a) is selected: Select a non-rate-responsive pacing sub-branch of the questioning sequence. Present Question 3.

Action in response to Answer 2 if (b) is selected: Select a rate-responsive pacing sub-branch of the questioning sequence. Present Question 3.

Question 3: What is the patient's age?

Answer 3: (the patient's age)

Action in response to Answer 3: Determine low rate limit (LRL), activate atrial tachycardia response (ATR, allowing pacing mode to switch from a dual-chamber mode to a single chamber mode, such as from DDD mode to VVI mode, the atrial tachycardia is detected), determine atrioventricular delay (AVD), etc., based on at least the patient's age and the patient's intrinsic parameters such as the heart rate and intrinsic AV interval measured from electrograms acquired by the pacemaker. Present Question 4.

Question 4: Does the patient have heart block?

Answer 4: (a) Yes, (b) No.

Action in response to Answer 4 if (a) is selected: Present Question 6.

Action in response to Answer 4 if (b) is selected: Present Question 5.

Question 5: What degree of heart block does the patient have?

Answer 5: (a) First, (b) Second, (c) Third.

Action in response to Answer 5 if (a) is selected: Present Question 6.

Action in response to Answer 5 if (b) is selected: Select a dual chamber demand pacing mode (e.g., DDD or DDDR, depending on the sub-branch of the questioning sequence). Determine an AVD. Activate AV search (periodic check on whether the ventricle can contract on its own). Present Question 6.

Action in response to Answer 5, if (c) is selected: Select a dual chamber demand pacing mode (e.g., DDD or DDDR, depending on the sub-branch of the questioning sequence). Select an AVD that is substantially shorter than the patient's intrinsic AVD measured from electrograms acquired by the pacemaker. Activate dynamic AVD and post ventricular atrial refractory period (PVARP) adjustments in response to the patient's heart rate variations. Present Question 6.

Question 6: How would you like to manage sensing?

Answer 6: (a) Fixed, (b) Automatic Gain Control (AGC).

Action in response to Answer 6 if (a) is selected: Present questions for setting one or more sensitivities (thresholds for detecting cardiac events from electrograms) before programming the implanted pacemaker. Present Question 7.

Action in response to Answer 6 if (b) is selected: Present questions for setting one or more sensitivities (thresholds for detecting cardiac events) for electrogram sensing before programming the implanted pacemaker. Activate AGC to stabilize the electrogram amplitudes before detecting the cardiac events using the one or more sensitivities. Present Question 7.

Question 7: How would you like to manage the pacing amplitudes?

Answer 7: (a) Manual, (b) Autocapture.

Action in response to Answer 7 if (a) is selected: Present questions for setting one or more pacing amplitudes and pulse widths before programming the implanted pacemaker. Present Question 8.

Action in response to Answer 7 if (b) is selected: Select autocapture (an automatic pacing threshold evaluation protocol executed to determine pacing thresholds including amplitudes and pulse widths). Present Question 8.

Question 8: Do you want atrial therapies?

Answer 8: (a) Yes, (b) No.

Action in response to Answer 8 if (a) is selected: Present questions for selecting atrial therapies, or ventricular therapies independent of atrial activities, that are available from the pacemaker.

(This question-and-answer session continues until values for a complete set of operational parameters required for the pacemaker to deliver bradycardia pacing therapy can be produced.)

Exemplary User Interface Screens

Figure 5:
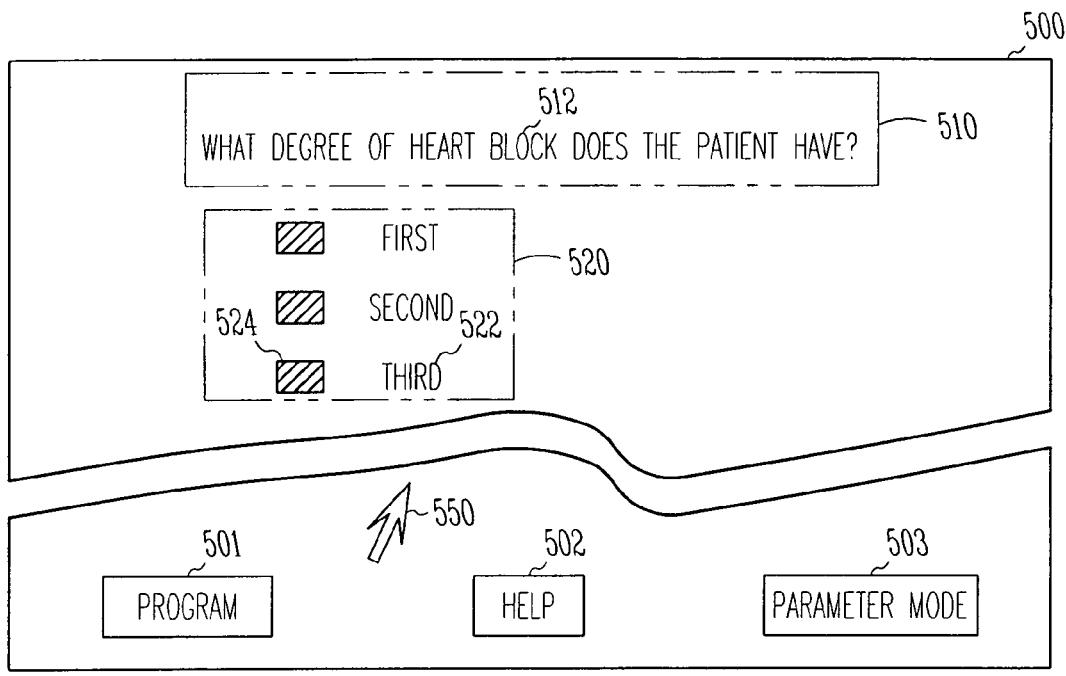
FIG. 5 is an illustration of an exemplary screen of a user interface of the device for programming the implantable medical device.
Figure 6:
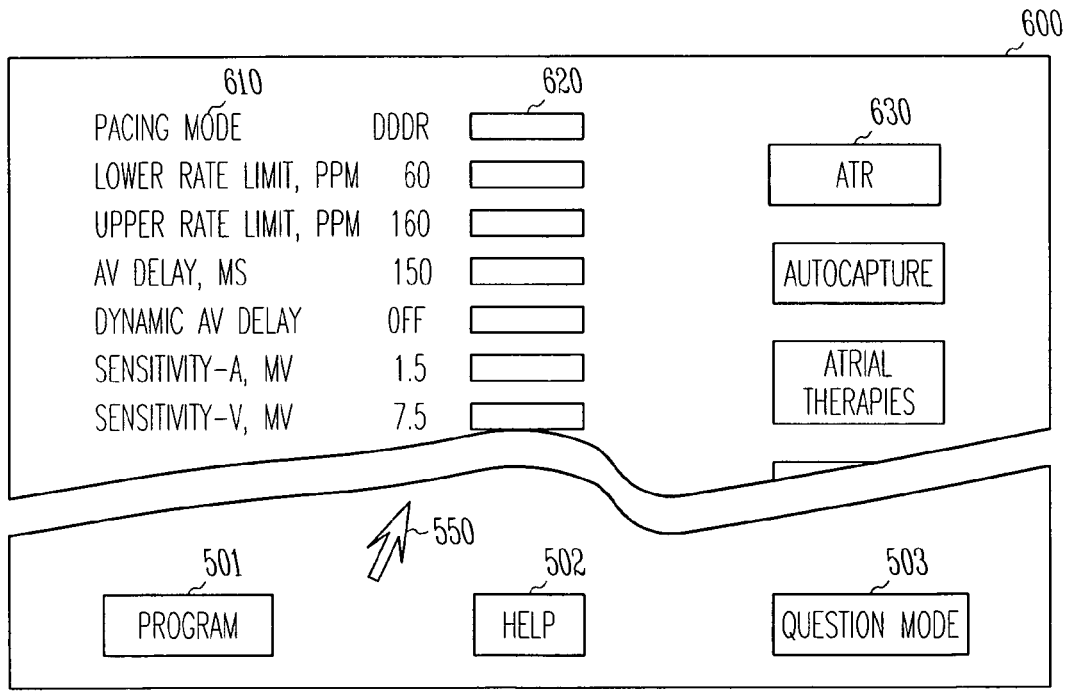
FIG. 6 is an illustration of another exemplary screen of the user interface of the device for programming the implantable medical device.

FIG. 5 shows an exemplary screen 500 illustrating one embodiment of portions of screen 244 when the question-based programming mode is selected. FIG. 6 shows an exemplary screen 600 illustrating one embodiment of portions of screen 244 when the parameter-based programming mode is selected. Screens 500 and 600 each include a programming button 501, a help button 502, a programming mode change button 503, and a cursor 550. Hitting programming button 501 starts a transmission of parameters and other data for programming implantable medical device 110. Hitting help button 502 causes a display of messages such as explanations of screen features and/or contents. Programming mode change button 503 is part of programming mode switch 242, which is a user controllable switch that allows the user to select one of the question-based programming mode (screen 500) and the parameter-based programming mode (screen 600) and to switch between the two modes during a programming session. On screen 500, programming mode change button 503 is labeled "Parameter Mode" and allows the user to switch from the question-based programming mode (screen 500) to the parameter-based programming mode (screen 600) by hitting it. On screen 600, programming mode change button 503 is labeled "Question Mode" and allows the user to switch from the parameter-based programming mode (screen 600) to the question-based programming mode (screen 500) by hitting it. It is to be understood that the content and layout of screens 500 and 600 as illustrated in FIGS. 5 and 6 are for illustrative purpose only. Any other screen design and layout are usable as long as the programming modes according to the present subject matter are accommodated.

Screen 500 includes a question field 510 and an answer field 520. A question 512 is displayed in question field 510, and a plurality of possible answers 522 are each displayed along with one of answer selection buttons 524 in answer field 520. The user selects one answer from the plurality of possible answers 522 by hitting the corresponding answer selection button. After the user selects one of the answers, question 512 is replaced by the next question, and the plurality of possible answers 522 and answer selection buttons 524 are updated accordingly. Alternative forms of answer selection include, but are not limited to, hitting on an answer itself or selecting from a pull-down menu. For questions that allow multiple answers, the user selects one or more answers from the plurality of possible answers 522 by hitting one or more corresponding answer selection buttons. For questions asking for an answer that is not convenient to include in a predetermined list, such as the patient's age, answer field 520 includes an answer entry field allowing the user to enter the answer by typing or writing. In various embodiments, more than one question may be displayed concurrently. If the user does not understand any question and/or answer, hitting help button 502 pops up a help window displaying explanations.

Screen 600 displays a plurality of pacing parameters 610 each including its current parameter value. Parameter value entry fields 620 allow the user to enter new parameter values to replace corresponding current parameter values. Screen 600 also displays special function buttons 630. Hitting one of the special function buttons 630 activates the function associated with that button or causes a programming field or window to be displayed to allow programming of implantable medical device 110 to perform that function.

The user may program implantable medical device 110 by using both screens 500 and 600, i.e., using both the question-based programming mode and the parameter-based programming mode. For example, the user may choose the question-based programming mode and complete a question-and-answer session with screen 500. After the question-and-answer session is completed, the user hits programming mode change button 503 to switch to screen 600, on which the current values are generated as the result of the programming in the question-based programming mode. The user confirms the values, made adjustment when deemed necessary or appropriate, and hits program button 501 to program the implantable medical device.

In General

It is to be understood that the above detailed description is intended to be illustrative, and not restrictive. For example, while a CRM system is specifically discussed in the description above, the present subject matter is generally applicable to various types of medical device systems. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A medical device programmer, comprising:
   a telemetry circuit adapted to communicate with an implantable medical device;
   a device identification device adapted to identify a device type of the implantable medical device using information received by the telemetry circuit from the implantable medical device, the device type indicative of one or more available operational modes of the implantable medical device;
   a user interface device including:
      a user-controllable programming mode switch configured to allow selection of a programming mode from a question-based programming mode and a parameter-based programming mode and allow the programming mode to be switched from the question-based programming mode to the parameter-based programming mode and from the parameter-based programming mode to the question-based programming mode during a programming session; and
      a screen including at least a question field and an answer field when the question-based programming mode is selected and a plurality of parameter value entry fields when the parameter-based programming mode is selected,
      wherein the user-controllable programming mode switch includes a programming mode change button displayed on the screen, the programming mode change button allowing the programming mode to be switched to the parameter-based programming mode when displayed during the question-based programming mode and switched to the question-based programming mode when displayed during the parameter-based programming mode; and
   a parameter generator coupled to the telemetry circuit, the device identification module, and the user interface, the parameter generator including an answer receiver to receive answers through the answer field of the screen and a parameter value receiver to receive parameter values through the parameter value entry fields and adapted to produce values for a set of operational parameters for the implantable medical device to operate in at least one operational mode of the one or more available operational modes using the received answers and the received parameter values.

2. The programmer of claim 1, wherein the device identification module comprises a device model identification device to identify a model number indicative of the device type.

3. The programmer of claim 1, wherein the device identification module comprises a device code identification device to identify a device code indicative of the device type.

4. The programmer of claim 1, wherein the user-controllable programming mode switch comprises a programming mode change button displayed on the screen.

5. The programmer of claim 1, wherein the answer field comprises means for selecting an answer from a plurality of predetermined possible answers.

6. The programmer of claim 1, wherein the parameter generator comprises a question-based parameter value generator and a parameter-based parameter value generator.

7. The programmer of claim 6, wherein the question-based parameter value generator comprises a questioning sequence selector to select a questioning sequence from one or more predetermined questioning sequences associated with the device type, the questioning sequence adapted to determine values of the set of operational parameters.

8. The programmer of claim 7, wherein the question-based parameter value generator further comprises:
   a question generator to generate questions to be displayed in the question field of the screen according to the selected questioning sequence; and
   the answer receiver,
   wherein the question generator generates one or more of the questions based on one or more answers received in response to one or more previously displayed questions.

9. The programmer of claim 8, wherein the question-based parameter value generator further comprises a question-based value producer to produce values for the set of operational parameters based on at least the received answers.

10. The programmer of claim 9, wherein the parameter-based parameter value generator comprises the parameter value receiver.

11. The programmer of claim 10, wherein the parameter-based parameter value generator further comprises a parameter-based value producer to produce one or more values for the set of operational parameters based on the received parameter values.

12. The programmer of claim 6, further comprising a parameter storage circuit, coupled to the parameter generator, the parameter storage circuit including:
   a nominal parameter storage circuit to store nominal parameter values for parameters of the implantable medical device, including the set of operational parameters; and
   a current parameter storage circuit adapted to store current parameter values of the set of operational parameters,
   wherein the current parameter storage circuit receives parameter values from the nominal parameter storage circuit and the parameter generator.

13. The programmer of claim 12, wherein the current parameter storage circuit comprises:
   a parameter initialization circuit to set each value of the current parameter values to a corresponding nominal parameter value; and
   a parameter update circuit to set each value of the current parameter values to a corresponding parameter value produced by the parameter generator.

14. A method, comprising:
   establishing communication with an implantable medical device;
   receiving information indicative of a device type of the implantable medical device from the implantable medical device, the device type indicative of one or more available operational modes of the implantable medical device;
   identifying the device type using the information indicative of the device type of the implantable medical device;
   presenting a programming mode switch on a screen during a parameter-based programming mode, the programming mode switch allowing for switching from the parameter-based programming mode to a question-based programming mode during a programming session;
   receiving one or more values each given to one parameter of a set of operational parameters during the parameter-based programming mode;
   receiving a user selection of a question-based programming mode using the programming mode switch;
   entering the question-based programming mode from the parameter-based programming mode in response to the user selection of the question-based programming mode;
   selecting a predetermined questioning sequence based on the device type;
   generating a first question according to the predetermined questioning sequence;
   presenting the first question;
   receiving a first answer to the first question;
   generating and presenting further questions and receiving further answers to the further questions according to the predetermined questioning sequence;
   generating values for the set of operational parameters based on at least the first answer and the further answers and the received one or more values, the set of operational parameters associated with at least one operational mode selected from the one or more available operational modes based on at least one answer of the first answer and the further answers.

15. The method of claim 14, wherein identifying the device type comprises identifying a device code indicative of the device type.

16. The method of claim 14, wherein identifying the device type comprises identifying a model number indicative of the device type.

17. The method of claim 14, wherein generating the first question comprises generating a question asking for the selection of the operational mode.

18. The method of claim 14, wherein generating further questions comprises generating one or more further questions each based on at least one answer to a preceding question.

19. The method of claim 14, wherein generating the values for the set of operational parameters comprises generating the values based on at least the first answer and the further answers and the one or more signals.

20. The method of claim 14, further comprising receiving one and more signals from the implantable medical device.

21. The method of claim 20, further comprising generating recommended answers to one or more of the first question and the further questions based on at least the one and more signals.

22. The method of claim 20, wherein generating the values for the set of operational parameters comprises generating the values based on at least the first answer and the further answers, the received one or more values, and the one and more signals.

23. The method of claim 14, further comprising receiving nominal values for the set of operational parameters.

24. The method of claim 23, wherein generating the values for the set of operational parameter values comprises generating the values based on at least the first answer and the further answers and the nominal values.

25. The method of claim 23, further comprising receiving one or more values from a user interface device, the one or more values each given to one parameter of the set of operational parameters, and wherein generating the values for the set of operational parameter values comprises generating the values based on at least the nominal values and the received one or more values.

26. The method of claim 14, further comprises transmitting the values of the set of operational parameters to the implantable medical device.

27. A method, comprising:
identifying a device type of an implantable medical device, the device type indicative of one or more available operational modes of the implantable medical device;
receiving from a user a selection of one of a question-based programming mode and a parameter-based programming mode;
displaying on a screen a programming mode change button, which allows for switching from the question-based programming mode to the parameter-based programming mode, and a sequence of questions with an answer field for each question to receive answers to the sequence of questions in response to a selection of the question-based programming mode;
displaying on the screen the programming mode change button, which allows for switching from the parameter-based programming mode to the question-based programming mode, and a plurality of parameter value entry fields to receive parameter values in response to a selection of the parameter-based programming mode; and
producing values for a set of operational parameters based on the answers to the sequence of questions and the received parameter values, the set of operational parameters associated with at least one operational mode selected from the one or more available operational modes.

28. The method of claim 27, wherein displaying the sequence of questions each with the answer field comprises presenting the sequence of questions each with a plurality of predetermined possible answers for selection.

29. The method of claim 27, wherein displaying the sequence of questions each with the answer field comprises selecting a questioning sequence from one or more predetermined questioning sequences based on the device type, the questioning sequence created for determining values of the set of operational parameters.

30. The method of claim 29, wherein displaying the sequence of questions each with the answer field further comprises generating the sequence of questions based on the selected questioning sequence and one or more answers received in response to one or more previously displayed questions.

31. The method of claim 30, further comprising creating each questioning sequence of the one or more predetermined questioning sequences based on a predetermined programming decision tree.

* * * * *

UNITED STATES PATENT AND TRADEMARK OFFICE
CERTIFICATE OF CORRECTION

PATENT NO. : 7,697,993 B2
APPLICATION NO. : 10/844642
DATED : April 13, 2010
INVENTOR(S) : James O. Gilkerson et al.

Page 1 of 1

It is certified that error appears in the above-identified patent and that said Letters Patent is hereby corrected as shown below:

In column 14, line 26, in Claim 14, after "sequence;" insert -- and --.

Signed and Sealed this

Fifteenth Day of June, 2010

David J. Kappos
*Director of the United States Patent and Trademark Office*